US012551650B2

(12) United States Patent
Roberts et al.

(10) Patent No.: US 12,551,650 B2
(45) Date of Patent: Feb. 17, 2026

(54) RESPIRATORY APPARATUS AIRFLOW TUBE

(71) Applicant: Exceleron Medical, LLC, St. Paul, MN (US)

(72) Inventors: Keith A. Roberts, Dellwood, MN (US); Charles Raskin, Blaine, MN (US)

(73) Assignee: Exceleron Medical, LLC, St. Paul, MN (US)

( * ) Notice: Subject to any disclaimer, the term of this patent is extended or adjusted under 35 U.S.C. 154(b) by 0 days.

(21) Appl. No.: 19/045,743

(22) Filed: Feb. 5, 2025

(65) Prior Publication Data

US 2025/0276147 A1 Sep. 4, 2025

Related U.S. Application Data

(60) Provisional application No. 63/734,927, filed on Dec. 17, 2024, provisional application No. 63/560,311, filed on Mar. 1, 2024.

(51) Int. Cl.
*A61M 16/08* (2006.01)
*A61M 16/00* (2006.01)
(Continued)

(52) U.S. Cl.
CPC .... *A61M 16/0875* (2013.01); *A61M 16/0003* (2014.02); *A61M 16/06* (2013.01);
(Continued)

(58) Field of Classification Search
CPC .......... A61M 16/0003; A61M 16/0051; A61M 16/0057; A61M 16/0066; A61M 16/021;
(Continued)

(56) References Cited

U.S. PATENT DOCUMENTS 4,686,354 A 8/1987 Makin
4,967,744 A * 11/1990 Chua .................. A61M 16/109 128/911

(Continued)

FOREIGN PATENT DOCUMENTS

AU 2014250602 B2 11/2014
CN 104784800 A 7/2015

(Continued)

OTHER PUBLICATIONS

Fisher & Paykel Healthcare, F&P Airspiral tube for less condensate, Apr. 30, 2021.

*Primary Examiner* — Annette Dixon
(74) *Attorney, Agent, or Firm* — Brian D. Kaul; Westman, Champlin and Koehler, P.A.

(57) ABSTRACT

A respiratory apparatus airflow tube configured to deliver an airflow from an airflow generator machine to a patient interface includes a flexible tube, a patient interface connector and a machine interface connector. The flexible tube includes a machine end, a patient end, and first and second heater wires extending from the machine end toward the patient end. The patient interface connector is attached to the patient end and is configured to attach to a patient interface. The machine connector is attached to the machine end and is configured to attach to an airflow generator machine. The machine connector includes an airflow housing having an interior wall defining an airflow pathway through which an airflow may be delivered into the machine end of the flexible tube and a temperature sensor located outside the airflow pathway.

21 Claims, 8 Drawing Sheets

(51) Int. Cl.
*A61M 16/06* (2006.01)
*A61M 16/10* (2006.01)
*A61M 39/10* (2006.01)

(52) U.S. Cl.
CPC .... *A61M 16/0816* (2013.01); *A61M 16/1095* (2014.02); *A61M 39/10* (2013.01); *A61M 2039/1022* (2013.01); *A61M 2202/0007* (2013.01); *A61M 2202/02* (2013.01); *A61M 2205/0216* (2013.01); *A61M 2205/0233* (2013.01); *A61M 2205/3331* (2013.01); *A61M 2205/3368* (2013.01); *A61M 2205/3653* (2013.01)

(58) Field of Classification Search
CPC .. A61M 16/06; A61M 16/0633; A61M 16/08; A61M 16/0816; A61M 16/0825; A61M 16/0833; A61M 16/0841; A61M 16/0875; A61M 16/1075; A61M 16/108; A61M 16/1085; A61M 16/109; A61M 16/1095; A61M 16/16; A61M 16/161; A61M 16/162; A61M 2016/0027; A61M 2016/0039; A61M 2016/1025; A61M 2202/0007; A61M 2202/0208; A61M 2202/03; A61M 2205/14; A61M 2205/3334; A61M 2205/3368; A61M 2205/3375; A61M 2205/3569; A61M 2205/3584; A61M 2205/3592; A61M 2205/3633; A61M 2205/3653; A61M 2205/6018; A61M 2205/6027; A61M 2205/6054; A61M 2230/04; F16L 11/12; F16L 11/127; F16L 11/24; F16L 53/38; G01K 13/02; G01K 13/024; H05B 2203/014; H05B 2203/017; H05B 2203/022; H05B 3/00; H05B 3/36; H05B 3/58; Y10S 128/911; Y10S 128/912
See application file for complete search history.

(56) References Cited

U.S. PATENT DOCUMENTS

| | | | | |
|---|---|---|---|---|
| 5,537,996 | A | 7/1996 | Mcphee | |
| 5,600,752 | A | 2/1997 | Lopatinsky | |
| 5,640,951 | A * | 6/1997 | Huddart | F16L 11/12 128/911 |
| 6,078,730 | A | 6/2000 | Huddart et al. | |
| 6,167,883 | B1 * | 1/2001 | Beran | H05B 3/00 128/203.17 |
| 6,691,707 | B1 | 2/2004 | Gunaratnam et al. | |
| 7,120,354 | B2 | 10/2006 | Mackie et al. | |
| 7,525,663 | B2 | 4/2009 | Kwok et al. | |
| 8,078,040 | B2 | 12/2011 | Forrester | |
| 8,459,259 | B2 | 6/2013 | Klasek et al. | |
| 8,733,349 | B2 | 5/2014 | Bath et al. | |
| 9,272,114 | B2 | 3/2016 | Herron | |
| 9,295,801 | B2 | 3/2016 | Graham et al. | |
| D762,843 | S | 8/2016 | Formica et al. | |
| 9,572,949 | B2 | 2/2017 | Vos et al. | |
| 9,784,387 | B2 | 10/2017 | Kaye et al. | |
| 9,855,398 | B2 * | 1/2018 | Klasek | A61M 16/0875 |
| 9,903,371 | B2 | 2/2018 | Row et al. | |
| 9,974,917 | B2 | 5/2018 | Bafile et al. | |
| 10,010,693 | B2 | 7/2018 | Sims | |
| 10,086,158 | B2 | 10/2018 | Bath et al. | |
| 10,195,388 | B2 | 2/2019 | Graham et al. | |
| 10,213,571 | B2 | 2/2019 | Coleman et al. | |
| 10,307,559 | B2 | 6/2019 | Foote et al. | |
| 10,363,382 | B2 | 7/2019 | Vos et al. | |
| 10,525,225 | B2 | 1/2020 | Seakins et al. | |
| 10,549,060 | B2 | 2/2020 | Foote et al. | |
| 10,688,270 | B2 | 6/2020 | Sims et al. | |
| 10,751,498 | B2 | 8/2020 | Munkelt et al. | |
| 10,828,455 | B2 | 11/2020 | Graham et al. | |
| 11,033,698 | B2 | 6/2021 | Bath et al. | |
| 11,052,215 | B2 | 7/2021 | Sims | |
| 11,065,414 | B2 | 7/2021 | Coleman et al. | |
| 11,116,931 | B2 | 9/2021 | Knepper et al. | |
| 11,135,391 | B2 | 10/2021 | Graham et al. | |
| 11,260,186 | B2 | 3/2022 | Vos et al. | |
| 11,311,695 | B2 | 4/2022 | Petrochenko et al. | |
| 11,504,492 | B2 | 11/2022 | Maurer | |
| 11,547,829 | B2 | 1/2023 | Knepper et al. | |
| 11,607,512 | B2 | 3/2023 | Bath et al. | |
| 11,707,587 | B2 | 7/2023 | Bath et al. | |
| 11,766,536 | B2 | 9/2023 | Peiris et al. | |
| 11,779,719 | B2 | 10/2023 | Vos et al. | |
| 11,844,905 | B2 | 12/2023 | Sims | |
| 11,911,563 | B2 | 2/2024 | Gibson et al. | |
| 12,011,543 | B2 | 6/2024 | Sims et al. | |
| 12,029,852 | B2 | 7/2024 | Lyon et al. | |
| 12,076,489 | B2 | 9/2024 | Petrochenko et al. | |
| 12,161,812 | B2 | 12/2024 | Graham et al. | |
| 2001/0017134 | A1 * | 8/2001 | Bahr | A61M 16/0816 128/204.18 |
| 2004/0182392 | A1 * | 9/2004 | Gerder | A61M 16/08 128/204.22 |
| 2005/0053368 | A1 * | 3/2005 | Pesu | A61L 9/037 392/390 |
| 2006/0037613 | A1 | 2/2006 | Kwok et al. | |
| 2010/0294280 | A1 | 11/2010 | Kratzenstein | |
| 2011/0108031 | A1 | 5/2011 | Korneff et al. | |
| 2012/0060836 | A1 | 3/2012 | El-Shammaa et al. | |
| 2014/0311487 | A1 * | 10/2014 | Buechi | A61M 16/021 128/203.14 |
| 2018/0214658 | A1 | 8/2018 | Forrester | |
| 2019/0344037 | A1 * | 11/2019 | Forrester | A61M 16/0833 |
| 2020/0206442 | A1 | 7/2020 | Knepper et al. | |
| 2020/0338295 | A1 | 10/2020 | Munkelt et al. | |
| 2021/0069447 | A1 | 3/2021 | Graham et al. | |
| 2021/0213233 | A1 | 7/2021 | Dwyer et al. | |
| 2021/0299392 | A1 | 9/2021 | Xu et al. | |
| 2021/0308409 | A1 | 10/2021 | Coleman et al. | |
| 2021/0322708 | A1 | 10/2021 | Moody et al. | |
| 2021/0379319 | A1 | 12/2021 | Chan | |
| 2022/0023581 | A1 | 1/2022 | Bath et al. | |
| 2022/0152325 | A1 | 5/2022 | Vos et al. | |
| 2022/0218934 | A1 | 7/2022 | Ozolins et al. | |
| 2022/0249798 | A1 | 8/2022 | Doudkine et al. | |
| 2022/0273895 | A1 | 9/2022 | Tatkov et al. | |
| 2022/0339390 | A1 | 10/2022 | Somervell et al. | |
| 2022/0355059 | A1 | 11/2022 | Holyoake et al. | |
| 2023/0046821 | A1 | 2/2023 | Maurer | |
| 2023/0140672 | A1 | 5/2023 | Klasek et al. | |
| 2023/0144677 | A1 | 5/2023 | McMahon et al. | |
| 2023/0149654 | A1 | 5/2023 | Newell et al. | |
| 2023/0218851 | A1 | 7/2023 | Forrester | |
| 2024/0042156 | A1 | 2/2024 | Liu et al. | |
| 2024/0058561 | A1 | 2/2024 | Peiris et al. | |
| 2024/0181198 | A1 | 6/2024 | Sims | |
| 2024/0189527 | A1 | 6/2024 | Bath et al. | |
| 2024/0269420 | A1 | 8/2024 | Thomas et al. | |
| 2024/0399097 | A1 | 12/2024 | Sims et al. | |

FOREIGN PATENT DOCUMENTS

| | | | |
|---|---|---|---|
| CN | 209575473 | U | 11/2019 |
| DE | 4039215 | A1 | 6/1992 |
| DE | 19958296 | C1 | 9/2001 |
| EP | 1858574 | B1 | 9/2010 |
| KR | 20210106748 | A | 8/2021 |
| WO | 2005021076 | A2 | 3/2005 |
| WO | 2022254214 | A1 | 12/2022 |
| WO | 2023242808 | A1 | 12/2023 |
| WO | 2024236257 | A1 | 11/2024 |

* cited by examiner

RESPIRATORY APPARATUS AIRFLOW TUBE

CROSS-REFERENCE TO RELATED APPLICATION

The present application is based on and claims the benefit of U.S. provisional patent application Ser. No. 63/560,311, filed Mar. 1, 2024, and U.S. provisional patent application Ser. No. 63/734,927, filed Dec. 17, 2024, the contents of which are hereby incorporated by reference in their entirety.

FIELD

Embodiments of the present disclosure relate to respiratory apparatuses that deliver an airflow to a patent through a patient interface, such as a mask, and more particularly to heatable airflow tubes through which the airflow is delivered to the patient.

BACKGROUND

Respiratory apparatuses are used to deliver breathable gas to a patient through a patient interface, such as a breathing mask. One such respiratory apparatus is a Continuous Positive Air Pressure (CPAP) unit, which may be used to provide pressure support therapy to a patient suffering from disordered breathing (e.g., sleep apnea, snoring, etc.) during sleep, in which a continuous positive air pressure to applied to the patient's airway. This positive air pressure effectively "splints" the airway, thereby maintaining an open passage to the lungs.

FIG. 11 is a simplified diagram of an example of a respiratory apparatus 200, such as a CPAP unit, in accordance with the prior art. The respiratory apparatus 200 includes an airflow generator machine 202 having an airflow generator 203 that generates an airflow 204 for a pressure support therapy that is delivered to a patient 206 through an airflow tube 208. The airflow tube 208 includes a flexible tube 210 having a machine interface or a machine connector 212 at a machine end 214, and a patient interface connector 216 at a patient interface end 218. The machine connector 212 connects to the airflow generator machine 202 and the patient interface connector 216 connects to a patient interface 220 (e.g., a mask). The airflow generator machine 202 may include a humidifier that humidifies the airflow 204 in order to reduce drying of the patient's airway and to improve patient comfort.

FIGS. 12 and 13 are simplified diagrams of example airflow tubes 208 of the prior art that include heater wires 222 and 224 extending in a spiral or helical manner within a wall of the flexible tube 210 from the machine end 214 to the patient interface end 218. A heater 226 (FIG. 11) of the respiratory apparatus 200 controls a heating current $I_h$ through the heater wires 222 and 224 to heat the flexible tube 210 and the airflow 204 traveling through the flexible tube 210 to improve patient comfort. Additionally, the heater 226 may heat the flexible tube 210 to prevent a "rain-out" condition, which occurs when moisture in the airflow 204 condenses on the inside of the flexible tube 210, such as when the flexible tube 210 is placed in a relatively cool environment.

Respiratory apparatuses utilizing the heatable airflow tube 208 conventionally include a temperature sensor 230 (e.g., thermistor) at the patient interface connector 216 that is used to sense the temperature of the airflow 204 prior to the patient interface 220. The heater 226 drives the heater current $I_h$ through the heater wires 222 and 224 based on a temperature signal from the temperature sensor 230 to maintain a desired airflow temperature (e.g., around 82-84° Fahrenheit) at the patient interface end 218 and to prevent a rain-out condition in the flexible tube 210.

The temperature signal is communicated to the heater 226 through at least one sensing wire, such as sensing wire 232 in the example airflow tube 208 shown in FIG. 12, or sensing wires 234 and 236 in the example airflow tube 208 shown in FIG. 13. The one or more sensing wires are typically integrated into the flexible tube 210 along with the heater wires 222 and 224. The temperature signal generally takes the form of a voltage (Vs) across the temperature sensor 230, such as a voltage between the sensing wire 232 and one of the heating wires (e.g., heating wire 224), as indicated in FIG. 12, or a voltage between the sensing wires 234 and 236, as indicated in FIG. 13.

Accordingly, the airflow tube 208 of the prior art typically includes three or more wires: two heater wires 222 and 224 and at least one sensing wire (232 or 234 and 236) that is connected to the temperature sensor 230 at the patient interface connector 216 or the patient interface end 218 of the airflow tube 208, as shown in FIGS. 11-13. The multiple wires in the airflow tube 208 increase the cost and complexity of the airflow tube 208 while decreasing the flexibility of the flexible tube 210. Examples of such airflow tubes 208 and corresponding respiratory apparatuses are described in U.S. Pat. No. 8,733,349 and U.S. Patent Application Publication No. US2021/0379319A1.

Furthermore, conventional means to control tubing temperature where the temperature is detected by the temperature sensor 230 at the patient interface connector 216 or the patient interface end 218 is significantly affected by the temperature of the airflow 204 but may also be affected by the exhalation breath of the patient. As a result, the temperature detected by the temperature sensor 230 may fluctuate in response to the patient's breathing, which may destabilize the control of the airflow tube heating.

Conventional airflow tubes also utilize patient interface connectors 216 that support the temperature sensor 230 within a structure 238 that protrudes into the airflow pathway 240 through which the airflow 204 travels, as shown FIG. 14, which is a simplified end view of the patient interface connector 216 of the airflow tube 208. The placement of the structure 238 in the airflow pathway 240 produces a pressure drop that reduces the pressure at the patient interface 220, increases the complexity of the patient interface connector 216 and increases manufacturing costs. As a result of the pressure drop associated with the protruding structure 238, the efficiency at which the airflow generator machine 202 provides a desired pressurized airflow 204 at the patient interface 220 is reduced resulting in higher power consumption.

SUMMARY

Embodiments of the present disclosure are directed to respiratory apparatus airflow tubes that are configured to deliver an airflow from an airflow generator machine to a patient interface and respiratory apparatuses that include the airflow tube. One embodiment of the airflow tube includes a flexible tube, a patient interface connector and a machine interface connector. The flexible tube includes a machine end, a patient end, and first and second heater wires extending from the machine end toward the patient end. The patient interface connector is attached to the patient end and is configured to attach to a patient interface. The machine connector is attached to the machine end and is configured to attach to an airflow generator machine. The machine connector includes an airflow housing having an interior wall defining an airflow pathway through which an airflow may be delivered into the machine end of the flexible tube and a temperature sensor located outside the airflow pathway.

In one embodiment, the machine connector includes an airflow tube electrical connector configured to connect to a machine electrical connector of the airflow generator machine. The airflow tube electrical connector includes a first electrical contact connected to the first heater wire, a second electrical contact connected to the second heater wire and a third electrical contact connected to the temperature sensor.

In one embodiment, the temperature sensor is connected in parallel with the second and third electrical contacts.

In one embodiment, the airflow tube electrical connector includes a fourth electrical contact connected to the temperature sensor, and the temperature sensor is connected in series with the third and fourth electrical contacts.

In one embodiment, t the temperature sensor is located on an exterior side of the airflow housing.

In one embodiment, the machine connector includes an airflow housing having an interior wall defining an airflow pathway through which an airflow may be delivered into the machine end of the flexible tube, and the temperature sensor is supported in the airflow pathway.

In one embodiment, the airflow tube includes an assembly that is attached to the airflow housing including the temperature sensor, a first conductor connected to the first heater wire, a second conductor connected to the second heater wire, a third conductor connected to the temperature sensor, and an airflow tube electrical connector. The airflow tube electrical connector is configured to connect to a machine electrical connector of the airflow generator machine and includes a first electrical contact connected to the first conductor, a second electrical contact connected to the second conductor, and a third electrical contact connected to the third conductor.

In one embodiment, the airflow housing includes an assembly connector that secures the electrical connector to the airflow housing.

One embodiment of the respiratory apparatus includes an airflow machine and an airflow tube. The airflow machine includes an airflow generator configured to drive an airflow through an output port, a heating unit and a heater controller. The airflow tube includes a flexible tube having a machine end, a patient end, and first and second heater wires extending from the machine end toward the patient end, a patient interface connector attached to the patient end and configured to attach to a patient interface, and a machine connector attached to the machine end of the flexible tube and connected to the output port. The machine connector includes an airflow housing having an interior wall defining an airflow pathway through which an airflow may be delivered into the machine end of the flexible tube and a temperature sensor located outside the airflow pathway. The heater controller is configured to control the heating unit to drive a current through the first and second heater wires using the temperature sensor.

In one embodiment, the airflow machine includes a machine electrical connector and the airflow tube includes an airflow tube electrical connector configured to connect to the machine electrical connector. The airflow tube electrical connector includes a first electrical contact connected to the first heater wire, a second electrical contact connected to the second heater wire, and a third electrical contact connected to the temperature sensor.

In one embodiment, the temperature sensor is connected across or in parallel with the second and third electrical contacts.

In one embodiment, the heater controller controls the current through the first and second heater wires based on a voltage between the second and third electrical contacts, which varies based on a temperature of the temperature sensor.

In one embodiment, the airflow tube electrical connector includes a fourth electrical contact connected to the temperature sensor, the temperature sensor is connected in series with the third and fourth electrical contacts, and the heater controller controls the current through the first and second heater wires based on a voltage between the third and fourth electrical contacts, which varies based on a temperature of the temperature sensor In one embodiment, t the temperature sensor is located on an exterior side of the airflow housing.

In one embodiment, the machine connector includes an airflow housing having an interior wall defining an airflow pathway through which the airflow is delivered into the machine end of the flexible tube, and the temperature sensor is supported in the airflow pathway.

In one embodiment, the airflow tube includes an assembly attached to the airflow housing. The assembly including the temperature sensor, a first conductor connected to the first heater wire, a second conductor connected to the second heater wire, a third conductor connected to the temperature sensor, and an airflow tube electrical connector connected to the machine electrical connector. The airflow tube electrical connector includes a first electrical contact connected to the first conductor, a second electrical contact connected to the second conductor, and a third electrical contact connected to the third conductor.

In one embodiment, the airflow housing includes an assembly connector that secures the electrical connector to the airflow housing.

In one embodiment, the respiratory apparatus includes a patient interface comprising a mask attached to the patient interface connector.

Another embodiment of the respiratory apparatus airflow tube includes a flexible tube including a machine end, a patient end, and first and second heater wires extending from the machine end toward the patient end, a patient interface connector attached to the patient end and configured to attach to a patient interface, and a machine connector attached to the machine end and configured to attach to an airflow generator machine. The machine connector includes a temperature sensor and an airflow tube electrical connector configured to connect to a machine electrical connector of the airflow generator machine. The airflow tube electrical connector including a first electrical contact connected to the first heater wire, a second electrical contact connected to the second heater wire, and a third electrical contact connected to the temperature sensor.

In one embodiment, the temperature sensor is connected in parallel with the second and third electrical contacts.

In one embodiment, the airflow tube electrical connector comprises a fourth electrical contact connected to the temperature sensor, and the temperature sensor is connected in series with the third and fourth electrical contacts.

In one embodiment, the machine connector includes an airflow housing having an interior wall defining an airflow pathway through which an airflow may be delivered into the machine end of the flexible tube, and the temperature sensor is located outside the airflow pathway.

In one embodiment, the machine connector includes an airflow housing having an interior wall defining an airflow pathway through which an airflow may be delivered into the machine end of the flexible tube, and the temperature sensor is supported in the airflow pathway.

Another embodiment of a respiratory apparatus airflow tube includes a flexible tube including a machine end, a patient end, and first and second heater wires extending from the machine end toward the patient end, a patient interface connector attached to the patient end and configured to attach to a patient interface, a machine connector attached to the machine end and configured to attach to an airflow generator machine, and a temperature sensor located along an airflow pathway extending through the machine connector, the flexible tube and the patient interface at a location that is closer to the machine connector than the patient interface connector.

In one embodiment, the temperature sensor is supported in the airflow pathway.

In one embodiment, the temperature sensor is supported outside the airflow pathway.

In one embodiment, the machine connector includes the temperature sensor.

In one embodiment, the flexible tube includes the temperature sensor.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
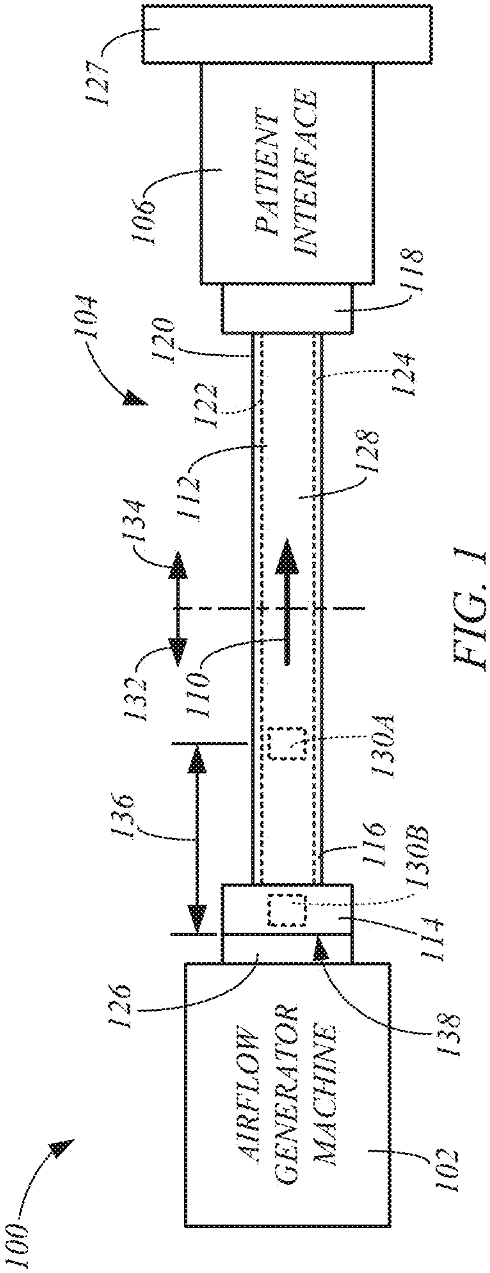
FIG. 1 is a simplified diagram of an example of a respiratory apparatus, in accordance with embodiments of the present disclosure.

Embodiments of the present disclosure are described more fully hereinafter with reference to the accompanying drawings. Elements that are identified using the same or similar reference characters refer to the same or similar elements. The various embodiments of the present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art.

It will be understood that when an element is referred to as being "connected," "coupled," or "attached" to another element, it can be directly connected, coupled or attached to the other element, or it can be indirectly connected, coupled, or attached to the other element where intervening or intermediate elements may be present. In contrast, if an element is referred to as being "directly connected," "directly coupled" or "directly attached" to another element, there are no intervening elements present. Drawings illustrating direct connections, couplings or attachments between elements also include embodiments, in which the elements are indirectly connected, coupled or attached to each other.

FIG. 1 is a simplified diagram of an example of a respiratory apparatus 100, in accordance with embodiments of the present disclosure. In one example, the respiratory apparatus 100 is in the form of a Continuous Positive Air Pressure (CPAP) unit. Embodiments of the present disclosure may be applicable to other types of respiratory apparatuses, such as a ventilator, for example.

The respiratory apparatus 100 generally includes an airflow generator machine 102, an airflow tube 104, and a patient interface 106. The airflow generator machine 102 may be a conventional device that is configured to generate an airflow 110, such as an airflow for providing pressure support therapy for a patient, for example.

The airflow tube 104 includes a flexible tube 112, a machine connector 114 attached to a machine end 116 of the flexible tube 112 and a patient interface connector 118 attached to a patient interface end 120 of the flexible tube 112. In some embodiments, a pair of conventional resistive heater wires 122 and 124 (hereinafter "heater wires") extend through the flexible tube 112, such as in a spiraling or helical manner within a wall of the flexible tube 112. The machine connector 114 is configured to connect to an output port 126 of the airflow generator machine 102, through which the airflow 110 is discharged. The patient interface connector 118 is configured to attach to the patient interface 106, which may take on any suitable form, such as a full-face mask, nasal mask, oral-nasal mask, mouth mask, nasal prongs, cannula etc. Also, headgear may be utilized to comfortably support the patient interface end 120 and the patient interface 106 in a desired position on a patient 127. The airflow 110 discharged through the output port 126 is delivered to the patient interface 106 through an airflow pathway 128 that extends through the machine connector 114, the flexible tube 112 and the patient interface connector 118.

The airflow generator machine 102 delivers a heater current through the heater wires 122 and 124, such as a pulse width modulated (PWM) current, based on a temperature signal from a temperature sensor 130, which may take on any suitable form. In one example, the temperature sensor 130 comprises a thermistor (e.g., 5 Kohm or 10 Kohm thermistor), such as a negative temperature coefficient (NTC) thermistor, for example. Other examples of the temperature sensor 130 include a resistance temperature detector (RTD), a thermocouple, or another suitable temperature sensor.

The airflow tube 104 includes a machine side 132 and a patient interface side 134 of a mid-point along the airflow pathway 128. Thus, elements on the machine side 132 are located closer to the machine connector 114 and the airflow generator machine 102 than elements on the patient interface side 134, and elements located on the patient interface side 134 are located closer to the patient interface connector 118 and the patient interface 106 than elements on the machine side 132.

In one embodiment, the temperature sensor 130 is located proximate to the airflow generator machine 102 on the machine side 132 of the airflow tube 104, such as within a distance 136 of the terminating end 138 of the machine connector 114. Examples of the distance 136 include less than about 12 inches, less than about 8 inches, less than about 4 inches or less than about 2 inches from the terminating end 138.

In one embodiment, the flexible tube 112 includes or supports the temperature sensor 130, as indicated by temperature sensor 130A at a location that is on the machine side 132. Here, the temperature sensor 130A may be located outside the airflow pathway 128, such as on an exterior side of the flexible tube 112 or within a wall of the flexible tube 112, or within the airflow pathway 128, such as attached to an interior wall of the flexible tube 112 that defines a portion of the airflow pathway 128, for example.

In some embodiments, the machine connector 114 includes the temperature sensor 130, as indicated by the temperature sensor 130B. In one embodiment, the temperature sensor 130B is located outside the airflow pathway 128. In another embodiment, the temperature sensor 130B is located within the airflow pathway 128.

Figure 2:
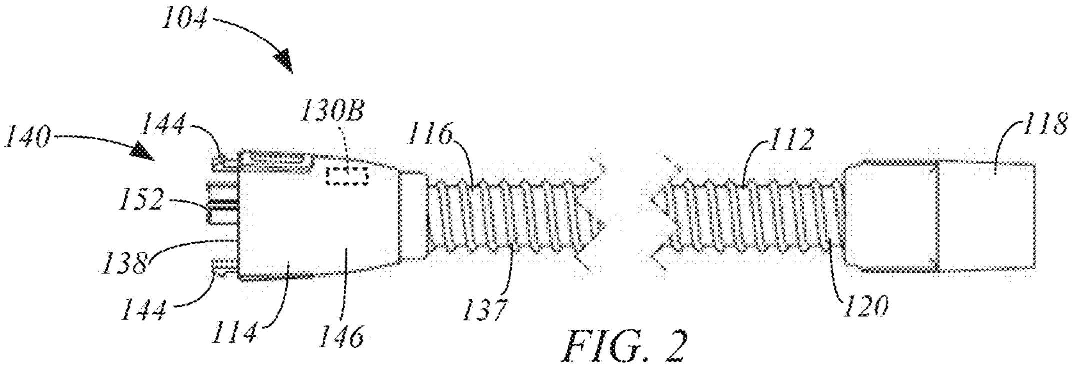
FIG. 2 is a side view of an example of an airflow tube, in accordance with embodiments of the present disclosure.
Figure 3:
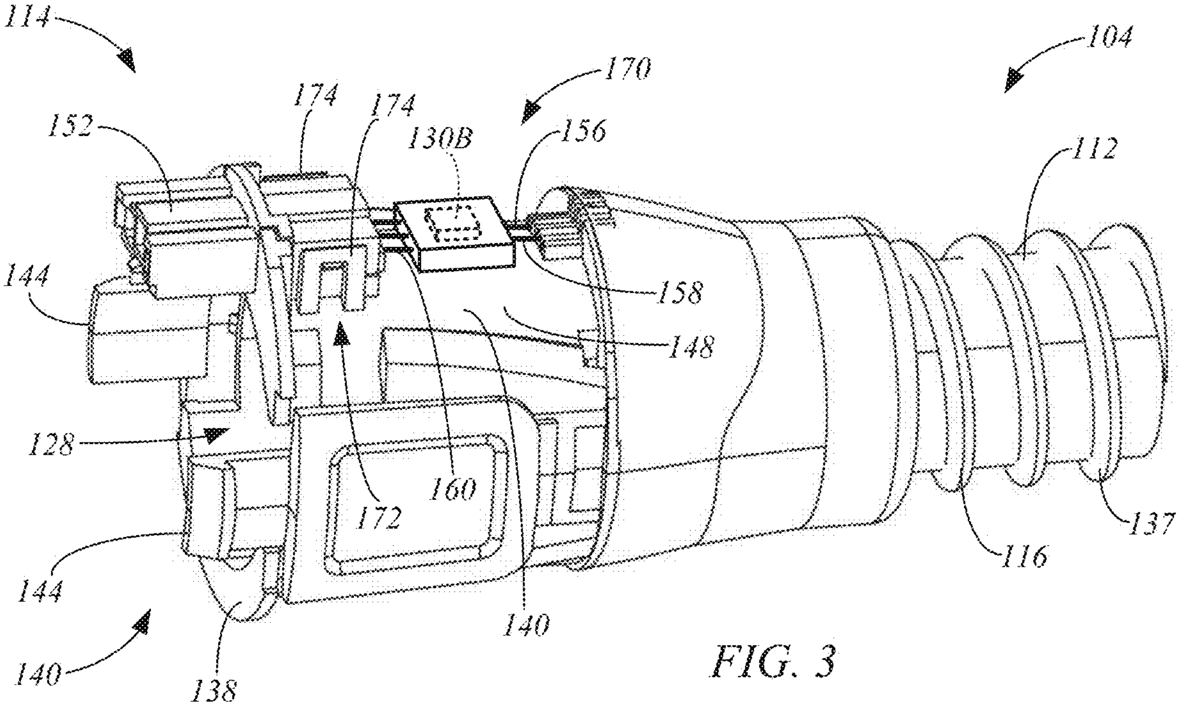
FIGS. 3, 4 and 5 respectively are isometric, top and front views of an example of a machine connector of an airflow tube, in accordance with embodiments of the present disclosure.
Figure 4:
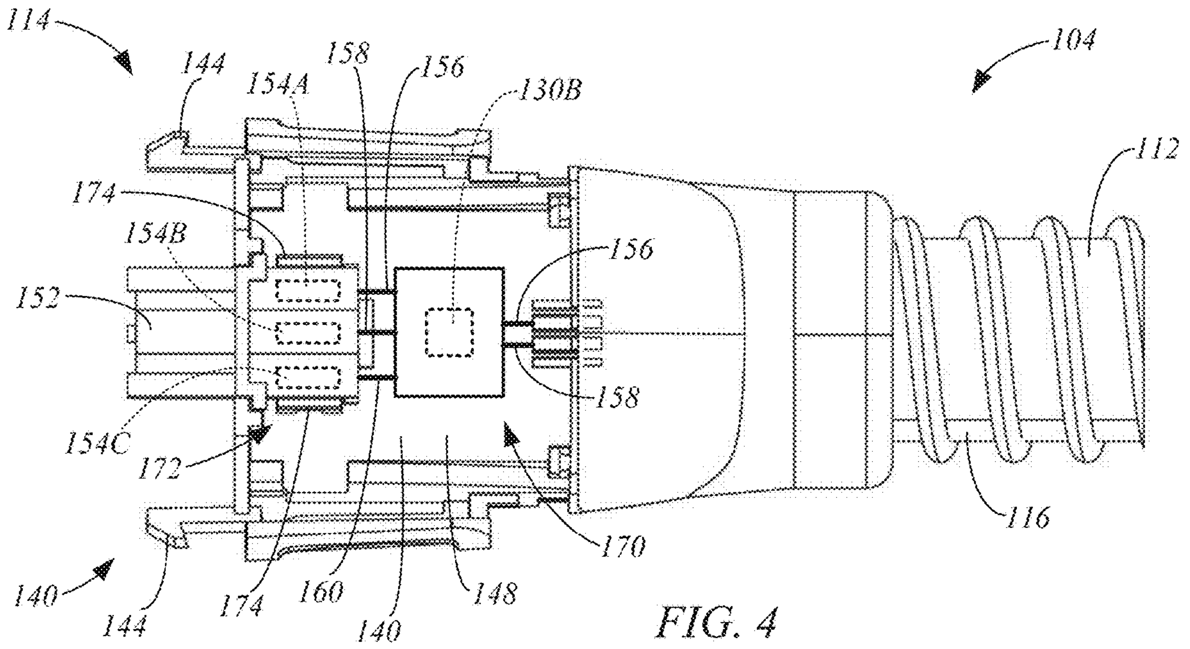
Figure 5:
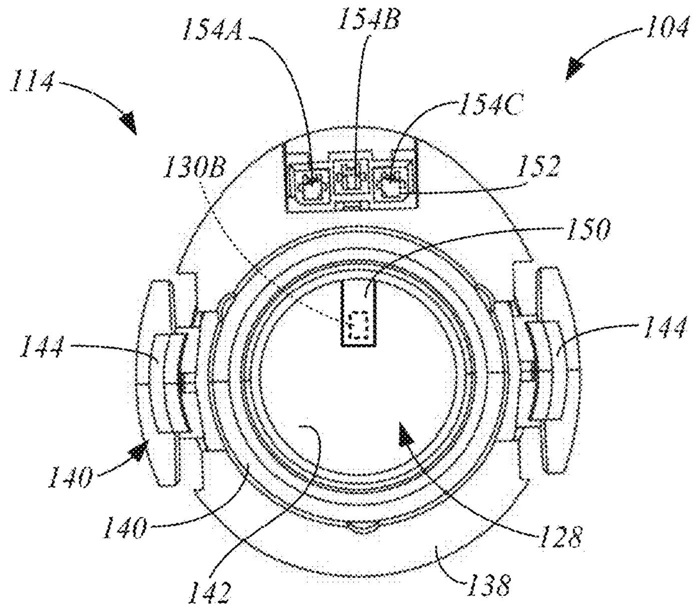

FIG. 2 is a side view of an example of the airflow tube 104, in accordance with embodiments of the present disclosure. FIGS. 3, 4 and 5 are isometric, top and front views of an example of the machine connector 114, in accordance with embodiments of the present disclosure. The flexible tube may include a wall having one or more helical ribs 137, and the heater wires may be contained within the one or more helical ribs 137.

Figure 14:
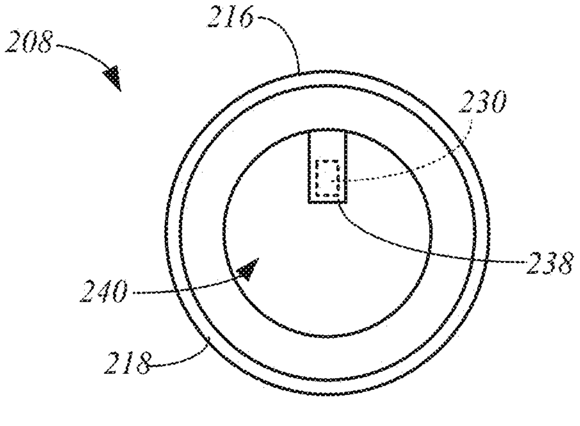
FIG. 14 (Prior Art)
FIG. 14 is a simplified end view of a patient interface connector of an airflow tube, in accordance with the prior art.

The patient interface connector 118 may comprise a conventional socket for connecting to a port or tube of the patient interface 106. The removal of the temperature sensor from the patient interface end 120 of the airflow tube 104 allows the patient interface end 120 and the patient interface connector 118 to be simplified relative to that of the prior art airflow tube 208, such as by eliminating the temperature sensor supporting structure 238 (FIG. 14) that protrudes into the airflow pathway 240 and produces a pressure drop that inhibits the airflow 204.

The machine connector 114 may include an airflow housing 140 that is connected to the machine end 116 of the flexible tube 112. The airflow housing 140 may be formed of rigid plastic, flexible polymers (e.g., thermoplastic elastomers), combinations of these materials or other conventional materials. The airflow housing 140 includes an interior wall 142 (FIG. 5) that defines the airflow pathway 128 through the machine connector 114. Conventional port connecting members 144, such as tabs that project from the terminating end 138 of the airflow housing 140 may cooperate with corresponding connecting members at the output port 126 of the airflow generator machine 102 to secure the machine connector 114 to the output port 126 and couple the airflow 110 discharged through the output port 126 to the airflow pathway 128 of the machine connector 114 and the flexible tube 112. A cover 146 may extend over the airflow housing 140 and the temperature sensor 130B and coupled to the flexible tube 112, as shown in FIG. 2.

Embodiments of the machine connector 114 that include the temperature sensor 130B either support the temperature sensor 130B outside the airflow pathway 128 or within the airflow pathway 128 through attachment of the temperature sensor 130B to the airflow housing 140. In one example, the temperature sensor 130B is located outside the airflow pathway 128 by attaching or supporting the temperature sensor 130B on an exterior 148 of the airflow housing 140, as shown in FIGS. 3 and 4, such that the temperature sensor 130B or a circuit board supporting the temperature sensor 130B, is not exposed to the airflow 110, such as through an opening or "window" in the airflow housing 140. As a result, the temperature sensed by the temperature sensor 130B is not driven by the airflow 110. Rather, the temperature sensed by the temperature sensor 130B is substantially driven by the temperature of the surrounding air that is in direct contact with the temperature sensor 130B, as well as a current driven through temperature sensor 130B by the heating voltage during the heating of the airflow tube 104 and/or temperature sensing operations, for example.

In one embodiment, the temperature sensor 130B is located within the airflow pathway 128 by attaching the temperature sensor 130B to the interior wall 142 of the airflow housing 140 or by supporting the temperature sensor 130B within a thermally conductive structure 150 that is embedded in the interior wall 142 or protrudes into the airflow pathway 128 from the interior wall 142, as shown in FIG. 5, for example. Accordingly, the temperature of the temperature sensor 130B supported within the airflow pathway 128 is substantially driven by the airflow 110.

Figure 6:
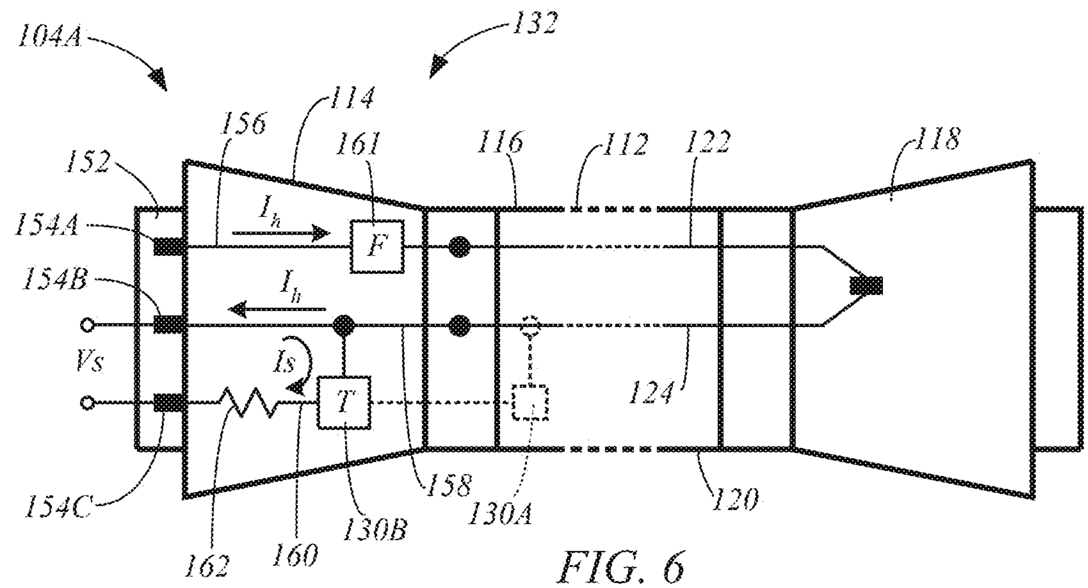
FIGS. 6 and 7 are simplified diagrams of example airflow tubes, in accordance with embodiments of the present disclosure.
Figure 7:
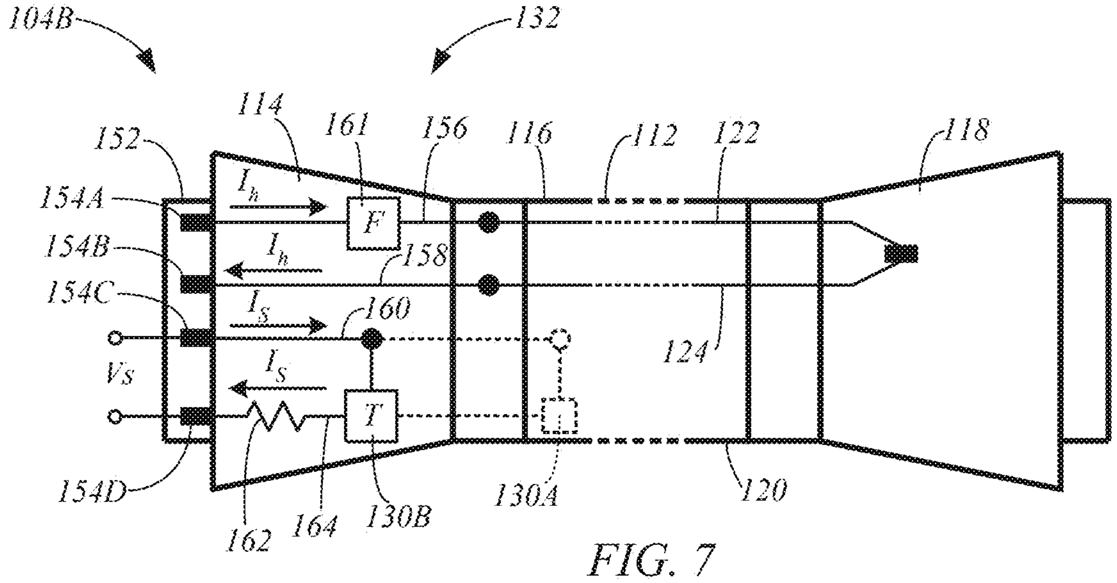

FIGS. 6 and 7 are simplified diagrams of airflow tubes 104A and 104B respectively having three and four electrical signal conductors, in accordance with embodiments of the present disclosure. Each of the airflow tubes 104A and 104B include the temperature sensor 130 on the machine side 132 of the flexible tube 112 as either a component of the machine connector 114 (temperature sensor 130B) or as a component of the flexible tube 112 (temperature sensor 130A). In some embodiments, the machine connector 114 includes an electrical connector 152 that connects to a corresponding connector of the airflow generator machine 102. The electrical connector 152 includes electrical contacts 154 that are each connected to an electrical signal conductor of the airflow tube 104, through which electrical signals, such as those generated by the airflow generator machine 102, are conducted.

The electrical connector 152 of the airflow tube 104A includes an electrical contact 154A that is connected to the heater wire 122 through a conductor 156, an electrical contact 154B that is connected to the heater wire 124 through a conductor 158, and an electrical contact 154C that is connected to the temperature sensor 130 through a conductor or sensor wire 160. In one embodiment, the temperature sensor 130 is connected in parallel between the electrical contact 154B and the electrical contact 154C using the sensor wire 160. In one embodiment, a self-resetting electrical fuse 161 may be placed in series with the heater wires 122 and 124 to open the circuit in the event of a short circuit, current spike (e.g., around 1.5-1.75 amps) or voltage spike through the heater wire 122 or 124, and self-reset when the fault condition is removed.

As mentioned above, the temperature sensor 130 may comprise a thermistor having a resistance that varies with its temperature. Thus, the temperature sensor 130 may have a "temperature signal" corresponding to its resistance, which may be determined based on a voltage Vs between the electrical contacts 154B and 154C, when a sense current $I_s$ conducted through the temperature sensor 130 and the electrical contacts 154B and 154C. A scaler resistance 162 (FIGS. 6 and 7) may be placed in series with the temperature sensor 130 to tune the temperature signal, if necessary, such that a desired voltage range for Vs is achieved in response to the sense current $I_s$ over a range of ambient temperatures.

During a heating operation, a heating current $I_h$ (e.g., PWM current) is conducted through the heater wires 122 and 124 and the electrical contacts 154A and 154B. The temperature signal (Vs) of the airflow tube 104 is typically sensed or measured by the airflow generator machine 102 during a period when the heating current $I_h$ is zero, in accordance with conventional techniques.

The electrical connector 152 of the airflow tube 104B may be formed similarly to the electrical connector of the airflow tube 104. For example, the electrical connector 152 of the airflow tube 104B may include the electrical contacts 154A and 154B that are respectively connected to the heater wires 122 and 124 through conductors 156 and 158. The electrical connector 152 of the airflow tube 104B also includes electrical contacts 154C and 154D that are dedicated to the temperature sensor 130. That is, the temperature sensor 130 and the scaler resistance 162 (if present) are connected in series with the electrical contacts 154C and 154D through conductors or sensor wires 160 and 164. This configuration allows for continuous or periodic monitoring of the temperature signal corresponding to the voltage Vs between the electrical contacts 154C and 154D using the sense current $I_s$, even while the heating current $I_h$ is conducted through the heater wires 122 and 124 and the electrical contacts 154A and 154B.

Figure 12:
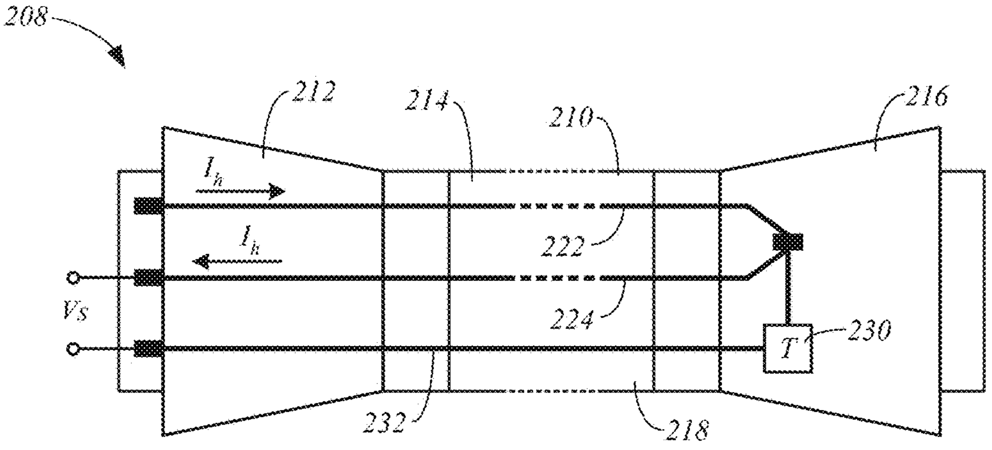
FIG. 12 (Prior Art)
FIGS. 12 and 13 are simplified diagrams of example airflow tubes, in accordance with the prior art.
Figure 13:
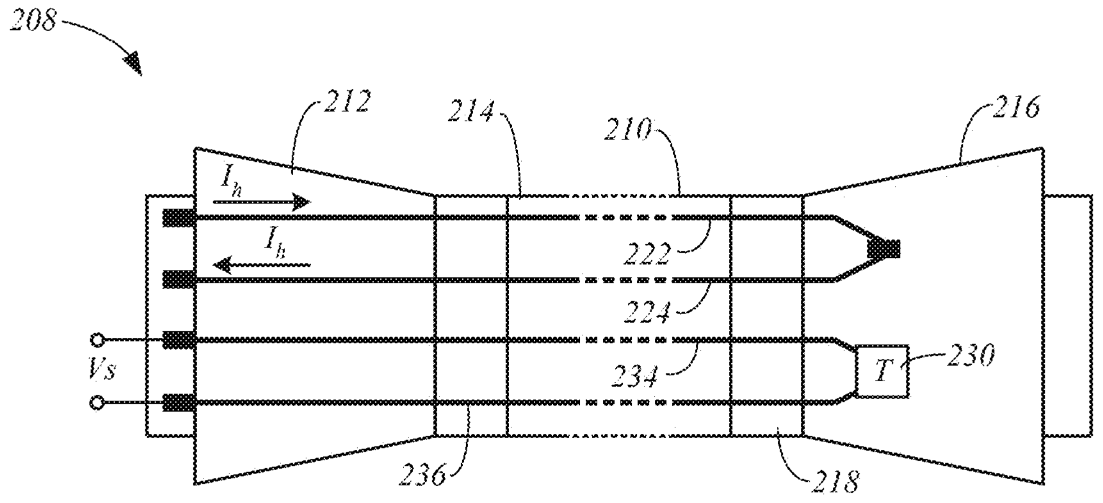
FIG. 13 (Prior Art)

Accordingly, locating the temperature sensor 130 on the machine side 132 of the airflow tube 104 allows the one or more sensor wires (160 and 164) that are connected to the temperature sensor 130 to be completely eliminated from the flexible tube unlike the sensor wires (232, 234 and 236) of the airflow tubes 208 of the prior art, or at least formed shorter than the sensor wires in the flexible tube of the airflow tubes 208 (FIGS. 12 and 13). For example, when the electrical connector 152 includes the temperature sensor 130, the only electrical signal conductors or wires included in the flexible tube 112 may be the heater wires 122 and 124. Thus, in some embodiments, the flexible tube 112 consist of only two electrical signal conductors in the form of the heater wires 122 and 124, rather than the three or more electrical signal conductors of the flexible tubes of conventional airflow tubes that extend along the entire length of the flexible tube. As a result, the airflow tube 104 includes significant advantages over conventional airflow tubes.

For example, the airflow tube 104 according to embodiments of the present disclosure has a significantly reduce complexity relative to conventional airflow tubes having flexible tubes with three or more electrical signal conductors extending their entire length resulting in reduced manufacturing costs and lower cost to the end user, while also eliminating a potential source of malfunction, such as a breakage of one of the sensor wires due to bending or crimping of the flexible tube. Additionally, the reduced number of electrical signal conductors and length of the electrical signal conductors within the flexible tube 112 reduces the weight of the airflow tube 104, improves its flexibility over its entire length or over the patient interface side 134, thereby simplifying and improving use of the airflow tube 104. Eliminating the sensor wires in the flexible tube 112 also increases patient safety by eliminating a source of electrical interference generated by the long sensor wires found in the airflow tubes 208 of the prior art, which can be hazardous to patients with pacemakers or other electronic implantable devices.

Furthermore, due to the location of the temperature sensor 130 on the machine side 132 of the airflow tube 104, such as the temperature sensor 130B on the machine connector 114 supported outside the airflow pathway 128, which may be 3-4 feet or more from the patient interface end 120 for an airflow tube 104 having a length of 6 feet, the temperature sensed by the temperature sensor 130 is not affected by the patient's breath or the airflow 110, which may not be the case in the conventional respiratory apparatus 200 having an airflow tube 208 in accordance with the prior art or at least a temperature sensor at the patient interface end 120. As a result, instability issues with the sensed temperature due to the patient's breath are avoided by the airflow tube 104, allowing for more stable and accurate temperature measurements and simplified control of the heating of the flexible tube 112.

In some embodiments, the three contact electrical connector 152 of the airflow tube 104A (FIG. 6), the temperature sensor 130, the conductors 156 and 158, and the sensor wire 160 form an assembly 170, such as shown in FIGS. 3 and 4. The assembly 170 simplifies manufacture of the airflow tube 104 by allowing an assembler to form the electrical circuit of the airflow tube 104 by connecting the conductor 156 to the heater wire 122 and connecting the conductor 158 to the heater wire 124 through a suitable conventional technique, such as soldering, for example, rather than having to connect each electrical contact 154 of the electrical connector 152 to its corresponding conductor when assembling the airflow tube 104. A similar assembly may be formed with the electrical connector 152 having four electrical contacts 154A-D, the conductors 156 and 158, and the sensor wires 160 and 164 of the airflow tube 104B (FIG. 7). Here the assembler must only connect the conductors 156 and 158 to the corresponding heater wires 122 and 124 to form the desired electrical circuit of the airflow tube 104.

In one embodiment, the airflow housing 140 includes an assembly connector 172 that allows an assembler to secure the assembly 170 to the airflow housing 140 by hand, as shown in FIGS. 3 and 4, to improve the efficiency at which the airflow tube 104 may be manufactured. For example, the assembly connector 172 may be located on the exterior of the airflow housing 140 and include tabs 174 or another suitable structure, in which a portion of the assembly 170, such as the electrical connector 152, may be pressed into by hand to secure the assembly 170 to the airflow housing 140.

Figure 8:
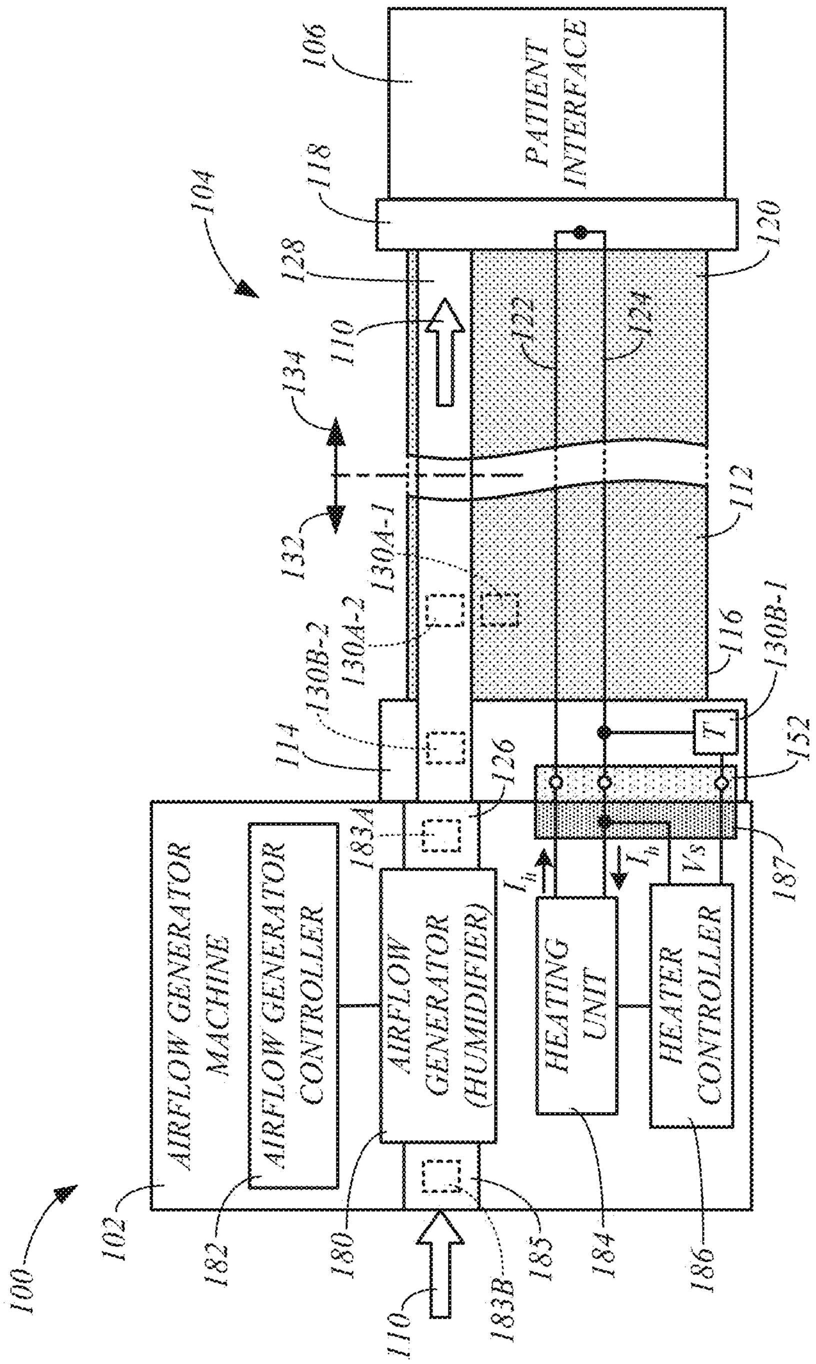
FIG. 8 is a simplified side view of a respiratory apparatus, in accordance with embodiments of the present disclosure.

FIG. 8 is a simplified side view of a respiratory apparatus 100, which includes an airflow generator machine 102 and the airflow generator airflow tube 104 formed in accordance with one or more embodiments described herein. In some embodiments, the airflow generator machine 102 includes an airflow generator 180 that is controlled by an airflow generator controller 182 to produce the desired airflow 110, in accordance with conventional respiratory apparatuses. Thus, the airflow generator 180 may comprise a conventional airflow generator (e.g., blower fan), such as that used in CPAP units, for example. The airflow generator 180 may also include a conventional humidifier for adding water vapor to the airflow 110 in response to control signals from the airflow generator controller 182.

The machine connector 114 of the airflow tube 104 connects to the airflow generator machine 180 at the output port 126, which directs the airflow 110 into the airflow pathway 128. The airflow 110 is delivered through the airflow pathway 128 of the machine connector 114, the flexible tube 112 and the patient interface connector 118, and is delivered to an attached patient interface 106.

The respiratory apparatus 100 also includes a heating unit 184 that is controlled by a heater controller 186 to drive the heating current $I_h$ through the heater wires 122 and 124 to heat the flexible tube 112 and the airflow 110 using the temperature sensor 130 that is located on the machine side 132 of the airflow tube 104. The temperature sensor 130 of the airflow tube 104 may take the form of a temperature sensor 130B-1 (solid lines) that is attached (e.g., directly attached) to the machine connector 114 and located outside the airflow pathway 128, such as temperature sensor 130B shown in FIG. 3, a temperature sensor 130B-2 that is attached (e.g., directly attached) to the machine connector 114 and contained in the airflow pathway 128, a temperature sensor 130A-1 that is attached (e.g., directly attached) to the flexible tube 112 and located outside the airflow pathway, or a temperature sensor 130A-2 that is attached (e.g., directly attached) to the flexible tube 112 and located within the airflow pathway 128.

In one embodiment, the heater controller 186 is controlled based on a temperature sensed by the temperature sensor 130B that is attached to or supported by the machine connector 114 outside the airflow pathway 128 and without using a temperature sensor that is configured to substantially directly measure the temperature of the airflow 110, such as using a temperature sensor that is supported in the airflow pathway or a temperature sensor that is exposed to the airflow 110 traveling through the airflow pathway 128, for example.

In some embodiments, the temperature sensor 130 may be replaced by a temperature sensor 183 that is upstream from the machine connector 114 and the airflow tube 104 relative to the airflow 110. For example, a temperature sensor 183A may be located at the output port 126 of the airflow generator 180 or a temperature sensor 183B may be located at an input port 185 of the airflow generator 180 through which the airflow is drawn. The temperature sensors 183A and 183B may be positioned either outside the airflow pathway through which the airflow 110 travels through the airflow generator 180 or within the airflow pathway through which the airflow 110 travels through the airflow generator 180. A temperature signal from the temperature sensor 183 may be used by the heater controller 186 to control the heating unit 184 in the same manner as the temperature signal Vs is used.

The heating unit 184 and the heater controller 186 may be connected to the heater wires 122 and 124, and the temperature sensor 130 through any of the configurations described herein. For example, the airflow generator machine 102 may include a machine electrical connector 187 that cooperates with the electrical connector 152 of the machine connector 114 to connect the heating unit 184 and the heater controller 186 to the contacts 154 of the electrical connector 152 and form an electrical circuit through which the heating current $I_h$ may be delivered through the heater wires 122 and 124 by the heating unit 184, and the temperature of the temperature sensor 130 may be sensed by the heater controller 186.

The airflow tube 104 shown in FIG. 8 includes the electrical connector 152 of the airflow tube 104A of FIG. 6 having three electrical contacts 154A-C. However, the airflow tube 104 may take the form of the airflow tube 104B of FIG. 7 having an electrical connector 152 that includes 4 electrical contacts 154A-D, or the airflow tube 104 may have another suitable electrical connector 152.

The heater controller 186 may sense the temperature of the temperature sensor 130 based on a temperature signal corresponding to a voltage (Vs) across the temperature sensor. The heater controller 186 may include conventional circuitry for processing the temperature signal (Vs) and comparing a value indicated by the temperature signal to values corresponding to the upper and lower limits of a set-point temperature range, such as that disclosed in U.S. Pat. No. 8,733,349, for example.

The heater controller 186 may be programmed based on empirical studies to control the heating unit 184 to deliver the proper amount of electrical power (heater current $I_h$) through the heater wires 122 and 124 based on the temperature indicated by the temperature signal Vs. That is, based on the set-point temperature range and the temperature indicated by the temperature signal, the heater controller 186 may control the heating unit 184 to deliver the electrical current $I_h$ (PWM current) through the heater wires 122 and 124 to heat the flexible tube 112 and the airflow 110 and/or prevent a rainout condition in the flexible tube 112.

Figure 9:
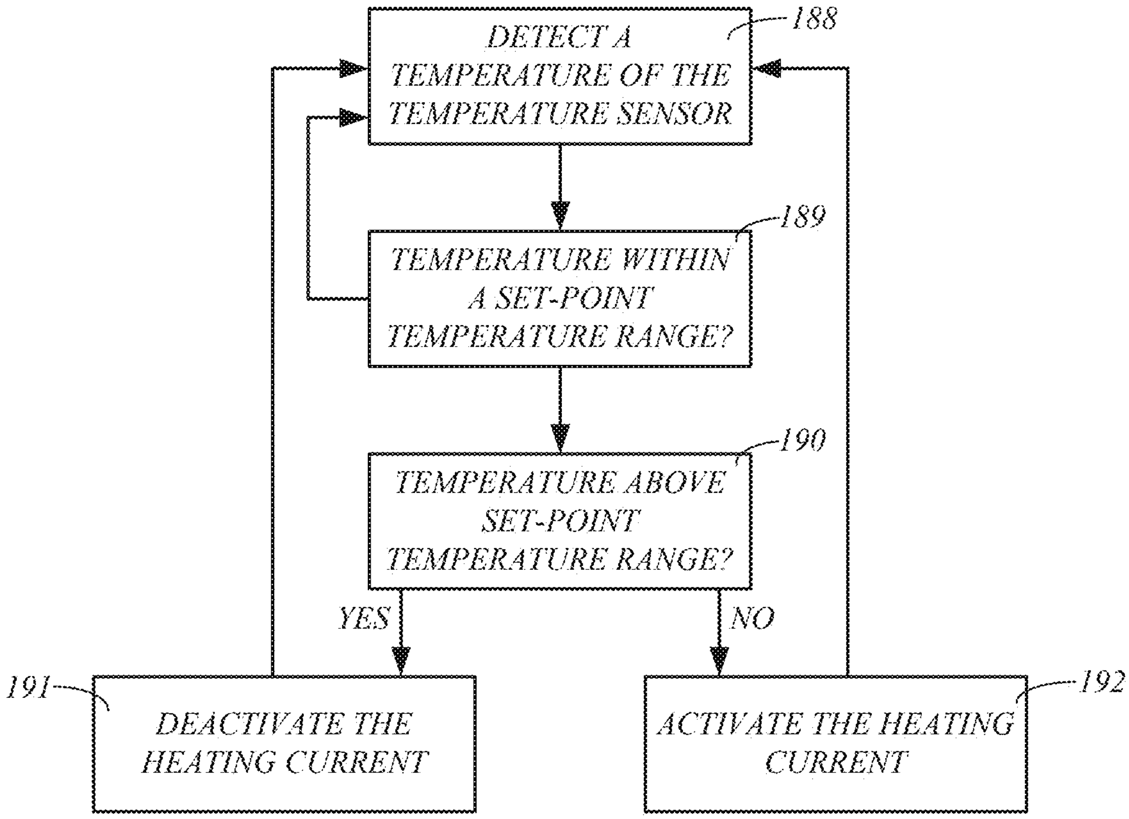
FIG. 9 is a flowchart of an example of a method of controlling airflow tube heating, in accordance with embodiments of the present disclosure.

FIG. 9 is a flowchart of an example of a method of controlling the heating of the airflow tube 104 using the heater controller 186, in accordance with embodiments of the present disclosure. When, for example, the airflow generator 180 of the respiratory apparatus 100 is activated, it produces the airflow 110 and the heater controller 186 detects a temperature of the temperature sensor 130 based on the temperature signal Vs, as indicated at 188. At 189, the heater controller 186 compares a value indicated by the temperature signal Vs, possibly after conventional processing by the electronics of the heater controller 186, to a set-point temperature range (e.g., upper and/or lower value limits). The set-point temperature range may be set by the user or determined and preset by medical personnel. The upper value limit of the set-point temperature range may be set to meet the appropriate safety requirements of the FDA. The separation between the lower and upper value limits of the range of set-point values is set to be sufficiently wide to prevent switching between heating and non-heating modes too often and too fast.

If the value indicated by the temperature signal is within the set-point temperature range, the method continues to monitor the temperature signal Vs by returning to step 188, such as after a predetermined delay.

If the value indicated by the temperature signal Vs is not within the set-point temperature range, the heater controller 186 determines whether the value indicates a temperature that is above or below the set-point temperature range at 190.

If the value indicated by the temperature signal Vs is higher than the set-point temperature range (e.g., upper value limit), the heater controller 186 may deactivate the heating current $I_h$, such as by terminating power to the heating unit 184, as indicated at 191.

If the value indicated by the temperature signal Vs is lower than the set-point temperature range (e.g., lower value limit), the heater controller 186 controls the heating unit to deliver a current $I_h$ through the heater wires 122 and 124, as indicated at 192. The electrical power delivered by the current $I_h$ may be increased or decreased based on a difference between the value indicated by the temperature signal Vs and the setpoint temperature range, in accordance with conventional techniques.

When the heating unit 184 is powered by direct current (DC) voltage, the heater controller 186 may adjust the current delivered through the heater wires 122 and 124 using Analog or pulse width modulation (PWM) control of the DC voltage and sense the temperature by sampling the temperature signal Vs (step 188) during a PWM off cycle. If an alternating current (AC) is used, the frequency and voltage level of the AC current through the heater wires 122 and 124 can be adjusted to provide the desired heating effect. As in any of the aforementioned cases, the temperature could be read in step 188 continuously or intermittently as needed to obtain the best temperature control requirement.

Following step 191 or 192, the method returns to step 188 and continues as described above, until the respiratory apparatus 100 is deactivated. A delay may be imposed before performing step 188 in order to allow the temperature to stabilize.

In some embodiments, the respiratory apparatus 100 may be configured to automatically set heater control parameters of the heater controller 186 and/or the airflow generator controller 182 based on a type of airflow tube 104 that is connected to the airflow generator machine 102, which may be identified based on a resistance of the temperature sensor 130 detected using the heater controller 186. As an example, a 15 mm internal diameter airflow tube 104 may include a temperature sensor 130 with a thermistor value of 10 kΩ and a 12 mm internal diameter heated tube may include a temperature sensor 130 with a thermistor value of 2 kΩ. Thus, the heater controller 186 and/or the airflow generator controller 182 may discriminate between different resistance values corresponding to the temperature sensor 130 that would indicate the diameter (e.g., 19 mm, 15 mm or 12 mm, etc.) and/or length of the airflow tube 104 in use to permit changes in the operation of the heater controller 186 and/or airflow generator controller 182 based on the type and characteristics of airflow tube 104 that is being used.

Thus, any compensation for air path performance (e.g., heating and temperature change of the airflow 110 from the machine end 116 to the patient interface end 120) can be adjusted automatically (without user intervention) for each type of airflow tube 104 by the heater controller 186, if required, such as electronically or through a look-up table based on the resistance of the temperature sensor 130 of the attached airflow tube 104. It should be appreciated that more than two types of tubes 104 may be detected by the airflow generator machine 102 using multiple comparator values, gains and thermistor styles. Detection of airflow tube types can also be used to allow amplifier gain designs provided by the electronics of the heater controller 186 to increase the amplitude of the temperature sense signals for a lower sensitivity (higher value NTC thermistor) circuit. This could also allow for adjustment in the airflow tube design of the signal gain so that the same tube may be used for different tube type requirements (i.e. different internal diameters).

Figure 10:
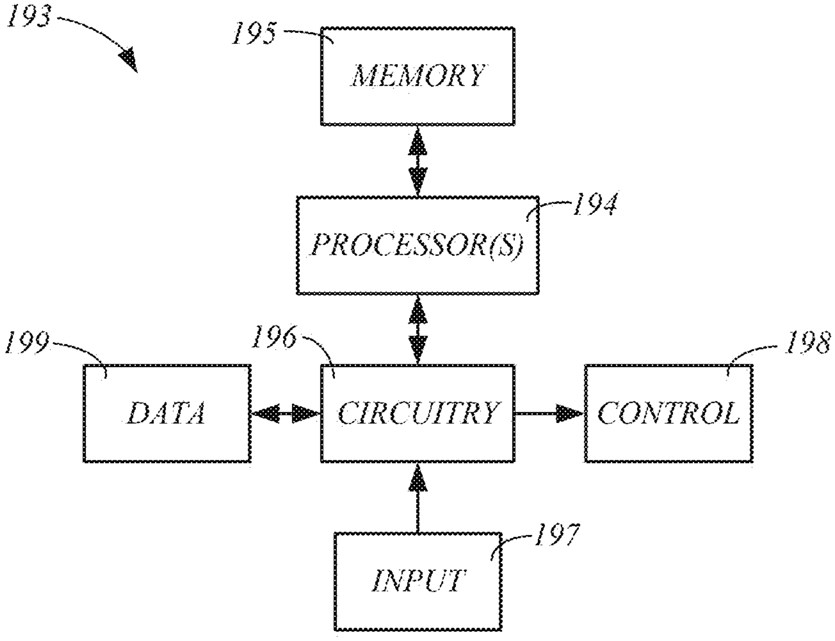
FIG. 10 is a simplified diagram of an example of a controller, in accordance with embodiments of the present disclosure.
Figure 11:
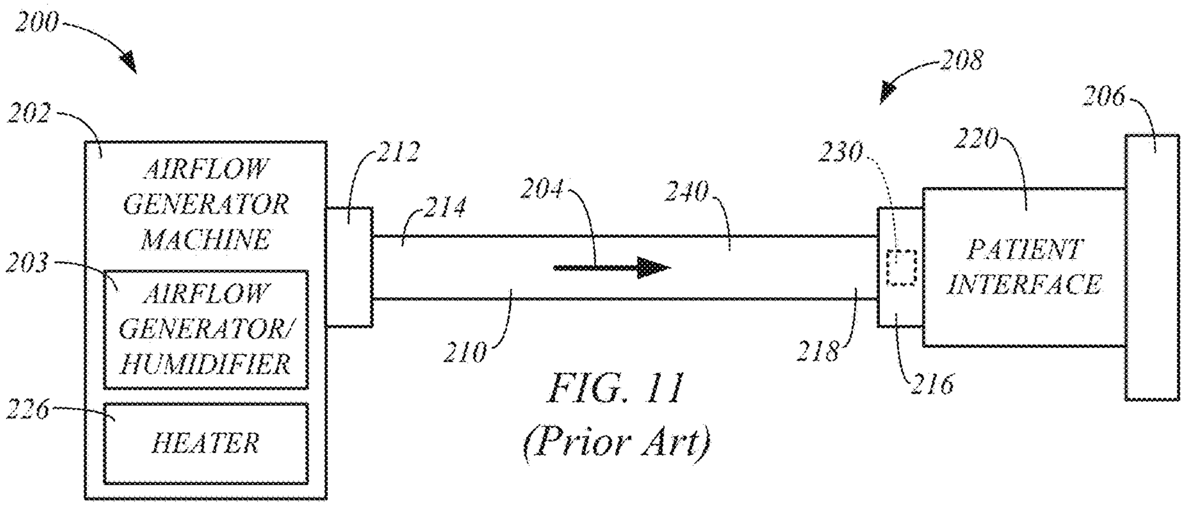
FIG. 11 (Prior Art)
FIG. 11 is a simplified diagram of an example of a respiratory apparatus, in accordance with the prior art.

The airflow generator controller 182 and the heater controller 186 may take on any suitable form, including the form of a single controller that performs their functions. A simplified diagram of an example of a controller 193 that may form the controller 182, the heater controller 186 or a combined controller, is shown in FIG. 10. The controller 193 may include one or more processors 194 and memory 195. The one or more processors 194 are configured to perform various functions (e.g., control of the airflow generator 180, control of the heating unit 184, etc.), in response to the execution of instructions contained in the memory 195.

The one or more processors 194 may be components of one or more computer-based systems, and may include one or more control circuits, microprocessor-based engine control systems, and/or one or more programmable hardware components, such as a field programmable gate array (FPGA). The memory 195 represents local and/or remote memory or computer-readable media. Such memory 195 comprises any suitable patent subject matter eligible computer readable media and does not include transitory waves or signals. Examples of the memory 195 include conventional data storage devices, such as hard disks, CD-ROMs, optical storage devices, magnetic storage devices and/or other suitable data storage devices. The controller 193 may include circuitry 196 for use by the one or more processors 194 to receive input signals 197 (e.g., airflow generator control signals, temperature signals, settings, etc.), issue control signals 198 (e.g., control signals for the airflow generator 180, the heating unit 184, etc.) and/or communicate data 199, such as in response to the execution of the instructions stored in the memory 195 by the one or more processors 194.

Although the embodiments of the present disclosure have been described with reference to preferred embodiments, workers skilled in the art will recognize that changes may be made in form and detail without departing from the spirit and scope of the present disclosure.

It will further be understood that any reference herein to known prior art does not, unless the contrary indication appears, constitute an admission that such prior art is commonly known by those skilled in the art to which the invention relates.

Specific details are given in the above-description to provide a thorough understanding of the embodiments. However, it is understood by those of ordinary skill in the art that the embodiments may be practiced without these specific details. For example, circuits, systems, networks, processes, frames, supports, connectors, motors, processors, and other components may not be shown, or may be shown in block diagram form in order to not obscure the embodiments in unnecessary detail.

As used herein, when one or more functions or process steps are described as being performed by a controller (e.g., a specific controller), one or more controllers, at least one controller, a processor (e.g., such as a specific processor), one or more processors or at least one processor, embodiments include the performance of the function(s) by a single controller or processor, or multiple controllers or processors, unless otherwise specified. Furthermore, as used herein, when multiple functions are performed by at least one controller or processor, all of the functions may be performed by a single controller or processor, or some functions may be performed by one controller or one processor, and other functions may be performed by another controller or processor. Thus, the performance of one or more functions by at least one controller or processor does not require that all of the functions are performed by each of the controllers or processors.

What is claimed is:

1. A respiratory apparatus airflow tube configured to deliver an airflow from an airflow generator machine to a patient interface, the airflow tube comprising:

a flexible tube including a machine end, a patient end, first and second heater wires extending from the machine end toward the patient end, and an airflow pathway extending within the flexible tube from the machine end to the patient end;

a patient interface connector attached to the patient end and configured to attach to a patient interface; and a machine connector attached to the machine end and configured to attach to an airflow generator machine, the machine connector including:

an airflow housing having an interior wall defining a portion of the airflow pathway; and a temperature sensor located outside the airflow pathway, wherein:

an airflow generated by the airflow generator machine travels through the airflow pathway including the airflow housing; and the temperature sensor is on an exterior side of the airflow housing.

2. The airflow tube according to claim 1, wherein the machine connector includes an airflow tube electrical connector configured to connect to a machine electrical connector of the airflow generator machine, the airflow tube electrical connector comprising:

a first electrical contact connected to the first heater wire;

a second electrical contact connected to the second heater wire; and a third electrical contact connected to the temperature sensor.

3. The airflow tube according to claim 2, wherein the temperature sensor is connected across the second and third electrical contacts.

4. The airflow tube according to claim 2, wherein:

the airflow tube electrical connector comprises a fourth electrical contact connected to the temperature sensor; and the temperature sensor is connected in series with the third and fourth electrical contacts.

5. The airflow tube according to claim 2, wherein the machine connector includes an electrical fuse in series with the first or second heater wire, wherein the electrical fuse is configured to block current flow through the first or second heater wire in the event of a current spike or a voltage spike through the first or second heater wire.

6. The airflow tube according to claim 1, including an assembly attached to the airflow housing comprising:

the temperature sensor;

a first conductor connected to the first heater wire;

a second conductor connected to the second heater wire;

a third conductor connected to the temperature sensor; and an airflow tube electrical connector configured to connect to a machine electrical connector of the airflow generator machine comprising:

a first electrical contact connected to the first conductor;

a second electrical contact connected to the second conductor; and a third electrical contact connected to the third conductor.

7. The airflow tube according to claim 6, wherein the airflow housing includes an assembly connector that secures the electrical connector to the airflow housing.

8. A respiratory apparatus comprising:

an airflow generator machine comprising:

an airflow generator configured to drive an airflow through an output port;

a heating unit; and a heater controller; and an airflow tube comprising:

a flexible tube having a machine end, a patient end, first and second heater wires extending from the machine end toward the patient end, and an airflow pathway extending within the flexible tube from the machine end to the patient end;

a patient interface connector attached to the patient end and configured to attach to a patient interface; and a machine connector attached to the machine end of the flexible tube and connected to the output port, the machine connector including:

an airflow housing having an interior wall defining a portion of the airflow pathway; and a temperature sensor located outside the airflow pathway, wherein:

an airflow generated by the airflow generator machine travels through the airflow pathway including the airflow housing;

the heater controller is configured to control the heating unit to drive a current through the first and second heater wires using the temperature sensor; and the temperature sensor is located on an exterior side of the airflow housing.

9. The apparatus according to claim 8, wherein:

the airflow machine includes a machine electrical connector;

the airflow tube includes an airflow tube electrical connector configured to connect to the machine electrical connector, the airflow tube electrical connector comprising:

a first electrical contact connected to the first heater wire;

a second electrical contact connected to the second heater wire; and a third electrical contact connected to the temperature sensor.

10. The apparatus according to claim 9, wherein the temperature sensor is connected across the second and third electrical contacts.

11. The apparatus according to claim 10, wherein the heater controller controls the current through the first and second heater wires based on a voltage between the second and third electrical contacts, which varies based on a temperature of the temperature sensor.

12. The apparatus according to claim 10, wherein the airflow tube includes an assembly attached to the airflow housing comprising:

the temperature sensor;

a first conductor connected to the first heater wire;

a second conductor connected to the second heater wire;

a third conductor connected to the temperature sensor; and an airflow tube electrical connector connected to the machine electrical connector, the airflow tube electrical connector comprising:

a first electrical contact connected to the first conductor;

a second electrical contact connected to the second conductor; and a third electrical contact connected to the third conductor.

13. The apparatus according to claim 12, wherein the airflow housing includes an assembly connector that secures the electrical connector to the airflow housing.

14. The apparatus according to claim 9, wherein:

the airflow tube electrical connector comprises a fourth electrical contact connected to the temperature sensor;

the temperature sensor is connected in series with the third and fourth electrical contacts; and the heater controller controls the current through the first and second heater wires based on a voltage between the third and fourth electrical contacts, which varies based on a temperature of the temperature sensor.

15. The apparatus according to claim 9, wherein the machine connector includes an electrical fuse in series with the first or second heater wire, wherein the electrical fuse is configured to block current flow through the first or second heater wire in the event of a current spike or a voltage spike through the first or second heater wire.

16. The apparatus according to claim 8, including a patient interface comprising a mask attached to the patient interface connector.

17. A respiratory apparatus airflow tube configured to deliver an airflow from an airflow generator machine to a patient interface, the airflow tube comprising:

a flexible tube including a machine end, a patient end, first and second heater wires extending from the machine end toward the patient end, and an airflow pathway extending within the flexible tube from the machine end to the patient end;

a patient interface connector attached to the patient end of the flexible tube and configured to attach to a patient interface; and a machine connector attached to the machine end of the flexible tube and configured to attach to an airflow generator machine, the machine connector including:

an airflow housing having an interior wall defining a portion of the airflow pathway;

a temperature sensor;

an electrical connector comprising:

a first heater wire contact;

a second heater wire contact;

a first temperature sensor contact; and a second temperature sensor contact;

a first conductor connecting the first heater wire contact to the first heater wire;

a second conductor connecting the second heater wire contact to the second heater wire; and third and fourth conductors connecting the temperature sensor in series with the first and second temperature sensor contacts.

18. The respiratory apparatus according to claim 17, wherein:

an airflow generated by the airflow generator machine travels through the airflow pathway including the airflow housing; and the temperature sensor is located outside the airflow pathway.

19. A respiratory apparatus airflow tube configured to deliver an airflow from an airflow generator machine to a patient interface, the airflow tube comprising:

a flexible tube including a machine end, a patient end, first and second heater wires extending from the machine end toward the patient end, and an airflow pathway extending within the flexible tube from the machine end to the patient end;

a patient interface connector attached to the patient end and configured to attach to a patient interface;

a machine connector attached to the machine end and configured to attach to an airflow generator machine, the machine connector including:

an airflow housing having an interior wall defining a portion of the airflow pathway; and a temperature sensor located outside the airflow pathway; and an assembly attached to the airflow housing comprising:

the temperature sensor;

a first conductor connected to the first heater wire;

a second conductor connected to the second heater wire;

a third conductor connected to the temperature sensor; and an airflow tube electrical connector configured to connect to a machine electrical connector of the airflow generator machine comprising:

a first electrical contact connected to the first conductor;

a second electrical contact connected to the second conductor; and a third electrical contact connected to the third conductor, wherein an airflow generated by the airflow generator machine travels through the airflow pathway including the airflow housing.

20. The airflow tube according to claim 19, wherein the airflow housing includes an assembly connector that secures the electrical connector to the airflow housing.

21. A respiratory apparatus airflow tube configured to deliver an airflow from an airflow generator machine to a patient interface, the airflow tube comprising:

a flexible tube including a machine end, a patient end, first and second heater wires extending from the machine end toward the patient end, and an airflow pathway extending within the flexible tube from the machine end to the patient end;

a patient interface connector attached to the patient end and configured to attach to a patient interface; and a machine connector attached to the machine end and configured to attach to an airflow generator machine, the machine connector including:

an airflow housing having an interior wall defining a portion of the airflow pathway; and a temperature sensor located outside the airflow pathway, wherein:

an airflow generated by the airflow generator machine travels through the airflow pathway including the airflow housing;

the machine connector includes an airflow tube electrical connector configured to connect to a machine electrical connector of the airflow generator machine, the airflow tube electrical connector comprising:

a first electrical contact connected to the first heater wire;

a second electrical contact connected to the second heater wire; and a third electrical contact connected to the temperature sensor; and the machine connector includes an electrical fuse in series with the first or second heater wire, wherein the electrical fuse is configured to block current flow through the first or second heater wire in the event of a current spike or a voltage spike through the first or second heater wire.

* * * * *